United States Patent [19]
Miller

[11] Patent Number: 4,840,931
[45] Date of Patent: Jun. 20, 1989

[54] METHOD OF INDUCING SURFACE ENSEMBLES ON A METAL CATALYST

[75] Inventor: Steven S. Miller, Morgantown, W. Va.

[73] Assignee: The United States of America as represented by the United States Department of Energy, Washington, D.C.

[21] Appl. No.: 103,866

[22] Filed: Oct. 2, 1987

[51] Int. Cl.$^4$ .................. B01J 31/24; B01J 31/20; B01J 31/18; C07C 1/04
[52] U.S. Cl. .................. 502/162; 502/161; 502/167; 518/714; 518/715; 518/720
[58] Field of Search .................. 502/162, 167, 161; 518/714, 715, 718-724

[56] References Cited

U.S. PATENT DOCUMENTS 4,361,499 11/1982 Hargis et al. .................. 502/162
4,539,334 9/1985 Murchison .................. 518/719

OTHER PUBLICATIONS

Mechanism of Carbon Monoxide Substitution in Metal Carbonyl Radicals: Vanadium Hexacarbonyl and Its Phosphine-Substituted Derivatives, Shi et al., *J. Am. Chem. Soc.*, 106:71 (1984).
Kinetics and Mechanism of Lewis Base Induced Disproportionation of Vanadium Hexacarbonyl and Its Phosphine-Substituted Derivatives, Richmond et al., *J. Am. Chem. Soc.*, 106:76 (1984).
Modification of Chemisorption Properties by Electronegative Adatoms: $H_2$ and CO on Chlorided, Sulfided, and Phosphided Ni(100), Kiskinova et al., *Surf. Sci.*, 108:64 (1981).
Use of Absorption Entropy to Choose between Kinetic Mechanisms, and Rate Equations for Fischer-Tropsch Synthesis, Dadyburjor, *J. Catal.*, 82:489 (1983).
The Fischer-Tropsch Activity of Nickel-Zirconia, Bruce et al., *Appln. Catal.*, 4:353 (1982).
An Infrared Reflection-Absorption Study of CO Chemisorbed on Clean and Sulfided Ni(111)-Evidence for Local Surface Interactions, Trenary et al., *Surf. Sci.*, 157:512 (1985).
Summary Abstract: Correlation of Surface Electronic Properties and Poison/Promoter Effects on the Reactivity of NI(100), Houston et al., *J. Vac. Sci. Technol.*, A2 (2):882 (1984).
Kenetics of the Methanation of Carbon Monoxide on an Alumina-Supported Nickel Catalyst, Klose et al., *J. Catal.*, 85:105 (1984).
Kinetics, Isotope Effects, and Mechanism of the Hydrogenation of Carbon Monoxide on Supported Palladium Catalyst, Mori et al., *J. Phys. Chem.*, 87:3648 (1983).
Microscopic Model for the Poisoning and Promotion of Absorption Rates by Electronegative and Electropositive Atoms, Norskov et al., *Surf. Sci.*, 137:65 (1984).
A Comprehensive Mechanism for the Fischer-Tropsch Synthesis, Rofer-DePoorter, *Chem. Rev.*, 81:447 (1981).
Catalytic Reduction of Carbon Monoxide Over Potassium Modified Iron Surfaces, Dwyer et al., *App. Surf. Sci.*, 19:14 (1984).

*Primary Examiner*—Paul E. Konopka
*Attorney, Agent, or Firm*—Earl L. Larcher; Stephen D. Hamel; William R. Moser

[57] ABSTRACT

A method of inducing surface ensembles on a transition metal catalyst used in the conversion of a reactant gas or gas mixture, such as carbon monoxide and hydrogen into hydrocarbons (the Fischer-Tropsch reaction) is disclosed which comprises adding a Lewis base to the syngas ($CO + H_2$) mixture before reaction takes place. The formation of surface ensembles in this manner restricts the number and types of reaction pathways which will be utilized, thus greatly narrowing the product distribution and maximizing the efficiency of the Fischer-Tropsch reaction. Similarly, amines may also be produced by the conversion of reactant gas or gases, such as nitrogen, hydrogen, or hydrocarbon constituents.

11 Claims, No Drawings

METHOD OF INDUCING SURFACE ENSEMBLES ON A METAL CATALYST

FIELD OF THE INVENTION

The invention relates generally to a method of inducing surface ensembles on a metal catalyst, and in particular to a method of inducing surface ensembles by use of a Lewis base so as to control the product distribution in the metal-catalyzed Fischer-Tropsch reaction which converts carbon monoxide and hydrogen gas into hydrocarbons.

BACKGROUND OF THE INVENTION

The use of catalytic processes in chemical reactions serves several purposes. Among these purposes are the lowering of barriers to a particular reaction (the "activation energy") so that the reaction can proceed under relatively mild conditions, and the shifting of dynamic equilibrium such as to increase the yield of a specific set of products which are kinetically disfavored under noncatalytic conditions. Once a catalytic system is implemented, it may be further fine-tuned by the use of promoters and/or inhibitors, such as those described in Norskov et al., Surf. Sci. 137: 65 (1984). It is highly desirable to be able to use these adspecies to promote the reactions leading to certain products, yet poison undesirable pathways at the same time.

One particularly important catalytic process is known as the Fischer-Tropsch reaction comprises the catalytic production of hydrocarbons and other oxygenated compounds from synthetic gases, specifically carbon monoxide (CO) and hydrogen gas ($H_2$). By this reaction, the efficient mass production of fuel is possible, and this fuel could provide a much needed alternative to the use of petroleum products. The importance of having a safe and productive domestic method of converting any combustible carbon-containing source into usable energy cannot be understated.

The major drawback in the mass production of fuel through the Fischer-Tropsch (or F-T) synthesis thus far has been the high statistical distribution of products which result from the reaction. In broadest terms, this reaction can be described as follows:

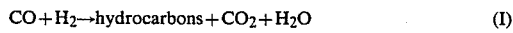
$$CO + H_2 \rightarrow hydrocarbons + CO_2 + H_2O \quad (I)$$

The F-T catalysts generally are chosen from the "d-block" of the periodic table, commonly known as the transition metals. The most commonly used of these metals for the reaction are iron, cobalt, nickel and ruthenium (as further described in Anderson, The Fischer-Tropsch Synthesis, Academic Press, Orlando, Fla., 1984).

The metal catalysts are employed in order to adsorb and then dissociate the $H_2$ and CO gases in the reactions indicated as follows:

$$H_2 + M \rightleftharpoons H-M-H \quad (II)$$

$$CO + M \rightleftharpoons M-CO \quad (III)$$

$$M-CO + M \rightleftharpoons M-C + M-O \quad (IV)$$

wherein M is the metal catalyst. Among the many possible pathways in the overall F-T reaction, the individual dissociated atoms can react with each other or with other compounds, leading to many possible products, just a few of which are indicated in the following reactions:

$$M-C + M-H \rightleftharpoons M-CH + M \quad (V)$$

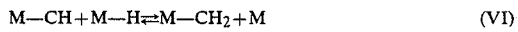
$$M-CH + M-H \rightleftharpoons M-CH_2 + M \quad (VI)$$

$$M-O + M-H \rightleftharpoons M-OH + M \quad (VII)$$

$$M-CO + M-H \rightleftharpoons M-CHO + M \quad (VIII)$$

$$M-CHO + M-H \rightleftharpoons M-CHOH + M \quad (IX)$$

These and other reactive pathways are desired in Rofer-DePoorter, Chem. Rev. 81: 447 (1981). Obviously, there are a larger number of products which can be produced in a Fischer-Tropsch synthesis.

The currently used catalytic systems allow for high selectivity only with regard to methane and methanol synthesis. If higher hydrocarbons are desired, one must be prepared to accept a distribution of products which includes both lighter and heavier hydrocarbon fractions along with the more desirable products. Oxygenated products (alcohols, ethers), branching, and degree of saturation all must be considered in determining the relative success of producing desired hydrocarbons from the synthetic gas.

Although major research efforts have been underway with the aim of narrowing the distribution of products, these efforts have had mixed levels of success. Included in these efforts are variation of supports, various poison/promoter combinations, and the use of molecular sieve-type zeolites. The zeolites generally are porous substrates in which the pores are windows which open into cavities or cages in the unit cell wherein the reaction takes place. These cages can thus hold the precursor syngas components and intermediates in configurations which can greatly narrow the product distribution and increase the potential for producing desired products. What has not yet been accomplished is the discovery of a way on a two-dimensional surface catalyst to configure the precursor species prior to the F-T reaction in order to enhance a narrow product distribution and ultimately provide for greater production of the desired hydrocarbons.

SUMMARY OF THE INVENTION

It has been discovered that surface ensembles which can hold precursor syngas components in configurations on metal catalyst surfaces so as to greatly narrow the product distribution in a Fischer-Tropsch reaction can be induced by the admixture of a Lewis base to the syngas mixtures. This ability of Lewis base-induced surface ensembles to lower product distribution will thus be of tremendous importance in the production of desired products, such as hydrocarbons from carbon monoxide and hydrogen gas or amines from nitrogen, hydrogen and/or hydrocarbon constituents using the transition metal-catalyzed Fischer-Tropsch synthesis.

DETAILED DESCRIPTION OF THE PREFERRED EMBODIMENTS

In accordance with the present invention, there is in one embodiment provided a method for inducing surface ensembles on metal catalysts during a Fischer-Tropsch reaction, wherein a metal-catalyzed conversion of carbon monoxide and hydrogen gas into hydrocarbons and other products takes place, comprising admixing a Lewis base with the carbon monoxide gas which is adsorbed by the metal catalyst. When admixed according to the present invention, the Lewis base-carbon monoxide admixture forms surface ensembles on the metal catalyst, and these surface ensembles are useful in controlling product distribution in the Fischer-Tropsch reaction.

A general Fischer-Tropsch reaction take place as follows:

$$nCO + mH_2 \rightarrow C_iH_jO_k + (n-i)CO_2 + (m-j/2)H_2O \qquad (X)$$

This reaction will normally produce a widespread distribution of products, not all of which are desirable. Product molecule distribution is a function dependent not only upon the specific catalyst and reaction conditions of the process, but upon the n:m ratio (in equation X above) as well. A fraction of the $CO_2$ found is the result of an implicit water-gas shift reaction as follows:

$$H_2O + CO \rightarrow H_2 + CO_2 \qquad (XI)$$

It would be of great economical advantage to limit the product distribution to a few favored constituents so as to save resources in terms of both feedstock consumption and product reprocessing.

One way to accomplish controls on product distribution in F-T synthesis is to configure the precursor species ($H_2$, CO) on the surface of the catalyst in such a way that only specific reactive pathways will be possible, and that the total product distribution will be greatly narrowed. It has been determined that a Lewis base, when admixed with the precursor species before reaction, will perturb the local work function of the metal lattice, and create ensembles of reactant species on the surface of the metal catalyst. These surface ensembles will thus restrict the reactant species and produce a narrow F-T product distribution.

The Lewis bases (electron donors) used in the method of the present invention most likely affect the conductive metal catalysts by modifying the electron density in the conduction band. The ease with which surface electron density may be used in the adsorption of reactive species depends upon the metal substrate's work function (an intrinsic property of the material). This work function may be modified by the donation or removal of electron density from the conduction band. In the case of F-T synthesis, this is very important for the dissociative adsorption of carbon monoxide. The ability of the substrate to "back-bond" into the 2pi* (antibonding) orbitals of the adsorbed CO molecule determines how strongly the molecule is held to the surface (increased by backbonding) and how readily it dissociates into reactive intermediates. Lewis bases tend to denote electrons into the conduction band, and thereby favor dissociative adsorption. Additionally, steric effects, or the blocking of sites, will further be responsible for the restriction on reactive species caused by the introduced Lewis base. The Lewis bases thus are able to induce surface ensembles which adjust equilibrium surface stoichiometry with respect to the partial pressure of gas-phase species, and thereby narrow product distribution in the F-T reaction.

In carrying out the method of the present invention, it is necessary to select a suitable transition metal to be used as the catalyst for the F-T reaction. Preferably, the metal catalyst will be comprised of iron, cobalt, nickel or a binary alloy of these metals. Other possible metal catalysts for use in F-T synthesis are molybdenum, vanadium, niobium and their alloys. Before the reaction is allowed to take place, it is preferred that the catalyst be cleaned of surface contaminants, such as by oxidation for several hours at temperatures of 800–1000 K. and at pressures of about 80–100 torr. This should be followed by several hours of hydrogen reduction at similar temperatures and pressures.

Any of a number of suitable gaseous Lewis bases can be employed to produce the metal surface ensembles in the F-T reaction. It is particularly desired that gaseous phosphines or phosphites, such as trimethylphosphite be employed, as these are easily handled, and, they behave as net electron-donors to the catalyst substrate. Other Lewis bases, such as nitriles, ethers, and pyridines, will also likely cause surface ensembles to form in the F-T synthesis, and thus will be usable in the present invention.

In another embodiment of the invention wherein a product such as amines are desirable, it is expected that the reactant mixture can be formed of nitrogen, hydrogen, or hydrocarbon constituents with a suitable Lewis base, such as described above.

The reaction can be initiated by placing the metal catalyst prepared above in an evacuated chamber cooled to room temperature. The metal catalyst can be of any form or configuration such as conventionally in catalysis. To this chamber is added an admixture of carbon monoxide (at around 10–12 torr) and the gaseous Lewis base, such as trimethylphosphite, at around 0.1–1.0 torr. Alternatively, the catalyst may be exposed to the Lewis base prior to the admixture with the reactant gas or gas mixtures. The admixture is absorbed by the metal foil until apparent equilibrium is reached. The chamber is then purged or evacuated and a fresh mixture of the CO/trimethylphosphite is admitted, if needed, and allowed again to come to equilibrium.

The appearance of surface ensembles has been evidenced by infrared spectroscopy at the two equilibrium points described above. Initially, competition between the CO and phosphite leads to high adsorption of the CO which inhibits phosphite adsorption. At the first equilibrium, spectroscopic tests showed a normal peak of adsorbed CO which gradually loses intensity as a new, more tightly bound state is generated as a consequence of phosphite adsorption. Subsequently, the phosphite is more slowly desorbed following the first purging or evacuation, resulting in the presence of gradually more mobile surface phosphite species. The second CO/phosphite mixture is then adsorbed on the remaining unoccupied sites, resulting in a substantial number of CO species adsorbed in the vicinity of the preadsorbed phosphite. This was confirmed by spectroscopic analysis showing a frequency shift in the CO bond indicative of increased bond strength caused by CO-phosphite surface ensembles.

Employing the concept of the present invention, one can thus use Lewis base gases to induce surface ensembles on metal catalysts which can tightly hold the precursor gases in a Fischer-Tropsch reaction. As a result, a much more narrow distribution of products of that reaction will be obtained, thus increasing the yield of desired products, and enhancing the potential utility of the Fischer-Tropsch synthesis in the production of domestic fuel supplies.

The following example is presented as illustrative of the present invention and should not be construed as limiting the scope of the invention in any way:

EXAMPLE

A manifestation of the desired surface ensemble induced by an admixed Lewis base has been observed in the lab. The experimental procedure producing this result has been performed in triplicate and comprises the following:

A nickel foil sample is oxidized as 850 K. for three hours at a relatively high pressure of 80-100 torr. This is immediately followed by a hydrogen reduction at similar pressures, and at a temperature of 925 K. This is continued overnight. The sample chamber is then evacuated and cooled to room temperature. A mixture of CO (10-12 torr) and trimethylphosphite (0.1-0.5 torr) is admitted to the chamber. The sample behaved as described in previous tests without the Lewis base, with a reduced intensity CO(adsorbed) resonance band observed at 2057 $cm^{-1}$ using Fourier-Transform Infrared Spectroscopy. With the passage of time, a new resonance not previously observed, at 2023 $cm^{-1}$ appears whilst that at 2057 $cm^{-1}$ is deminished in intensity. After apparent equilibrium is reached, the coil is evacuated and a fresh mixture of CO/phosphite is admitted into the cell. The second mixture is then removed by reevacuating the cell. Residual adsorbed phosphite existed on the nickel surface for some time after evacuation as evidenced as a C—O methoxy-type stretch as 1038 $cm^{-1}$. No CO of any type was observed at this point.

The evidence supplied by these tests points towards a scenario wherein an initial competition between the kinetic "product" of this reaction, CO (adsorbed), inhibits the adsorption of the phosphite. The phosphite, however, is apparently more slowly desorbed following evacuation, which results in the presence of a mobile surface phosphite species. The newly admitted second aliquot of the CO/phosphite mixture can then adsorb on the remaining unoccupied sites, resulting in a substantial number of CO species adsorbed in the vicinity of the now preadsorbed phosphite.

The evidence also points to the inducement of a Lewis base ensemble on the surface of the metal foil catalyst. First, the observed new resonance frequency only occurs in the presence of the trimethylphosphite (Lewis base) species, indicating that it is induced by a coadsorption phenomenon. Second, the frequency shift of $-30$ $cm^{-1}$ indicates a weakening of the CO triple bond by increased electron density in its pi* orbitals. This is always indicative of an increased bond strength between the metal surface and the CO adsorbed on the surface. The existence of two types of CO on the metal surface, one with the normal infrared adsorption frequency and one with a reduced infrared frequency can lead to only one reasonable scenario for the observed surface states: CO away from the phosphite is "normally" bound to the surface, while the CO within the neighborhood of the phosphite exhibits enhanced bonding to the surface due to the fact that it is held within a Lewis base-induced surface ensemble.

What is claimed is:

1. A method of inducing surface ensembles on metal catalysts for use in controlling product distribution in the metal-catalyzed conversion of carbon monoxide and hydrogen into hydrocarbons comprising confining a metal catalyst in an evacuated volume at about room temperature, contacting the metal catalyst with a mixture of a gaseous Lewis base and carbon monoxide having a carbon monoxide to Lewis base ratio in the range of about 10 to 120:1 to adsorb the mixture on the surface of the metal catalyst to create reactive ensembles of carbon monoxide on the surface of said catalyst provided by a substantial number of carbon monoxide species being adsorbed on said surface in the vicinity of adsorbed gaseous Lewis base species which tightly bind the carbon monoxide species to the surface of the metal catalyst.

2. A method according to claim 1 wherein the metal catalyst is cleansed of surface contaminants and subjected to hydrogen reduction prior to contact with said mixture.

3. A method according to claim 1 wherein the metal catalyst comprises a transition metal.

4. A method according to claim 3 wherein the metal catalyst is selected from the group consisting of iron, cobalt, nickel, molybdenum, vanadium, niobium, and alloys of these metals.

5. A method according to claim 1 wherein the metal catalyst is in the form of a metal foil.

6. A method according to claim 1 wherein the gaseous Lewis base is selected from the group consisting of phosphites, phosphines, nitriles, ethers, and pyridines.

7. A method according to claim 1 wherein the gaseous Lewis base is selected from the group consisting of phosphines and phosphites.

8. A method according to claim 1 wherein the gaseous Lewis base comprises trimethylphosphite.

9. A method according to claim 1 wherein said ratio of carbon monoxide to the gaseous Lewis base is provided in the evacuated volume by introducing therein about 10-12 torr of carbon monoxide and about 0.1-1.0 torr of the gaseous Lewis base.

10. A method according to claim 1, wherein the contact of the gaseous mixture with the surface of the metal catalyst is maintained until apparent equilibrium is reached.

11. A method according to claim 10, including the additional steps of evacuating the confined volume after reaching apparent equilibrium and thereafter contacting the metal catalyst with another mixture of a gaseous Lewis base and carbon monoxide in concentrations within said ratio to create additional ensembles of carbon monoxide on the surface of said catalyst.

* * * * *